United States Patent [19]
Franz

[11] 3,954,848
[45] May 4, 1976

[54] PROCESS FOR PRODUCING N-PHOSPHONOMETHYL GLYCINE
[75] Inventor: John E. Franz, Crestwood, Mo.
[73] Assignee: Monsanto Company, St. Louis, Mo.
[22] Filed: May 31, 1972
[21] Appl. No.: 258,281

[52] U.S. Cl. ............................................. 260/502.5
[51] Int. Cl.² ................................................ C07F 9/38
[58] Field of Search ................................. 260/502.5

[56] References Cited
UNITED STATES PATENTS

| | | | |
|---|---|---|---|
| 3,288,846 | 11/1966 | Irani et al. | 260/502.5 |
| 3,429,914 | 2/1969 | Crutchfield et al. | 260/502.5 |
| 3,796,749 | 3/1974 | Krueger et al. | 260/502.5 |

OTHER PUBLICATIONS

Van Wazer, "Phosphorus and its Compounds," Vol. 1 (1958), p. 379.

*Primary Examiner*—Joseph E. Evans
*Attorney, Agent, or Firm*—William T. Black; Donald W. Peterson

[57] ABSTRACT

N-phosphonomethyl glycine is produced by the oxidation of N-(phosphonomethyl) iminodiacetic acid in the presence of an acid. N-phosphonomethyl glycine is useful as a herbicide.

10 Claims, No Drawings

PROCESS FOR PRODUCING N-PHOSPHONOMETHYL GLYCINE

This invention relates to a method of producing N-phosphonomethyl glycine by the acid catalyzed oxidation-hydrolysis of N-(phosphonomethyl) iminodiacetic acid. More particularly, this invention relates to the production of N-phosphonomethyl glycine by the oxidation of N-(phosphonomethyl) iminodiacetic acid in an acid media, with an oxidizing agent such as hydrogen peroxide.

In accordance with the process of this invention, N-(phosphonomethyl) iminodiacetic acid having the formula

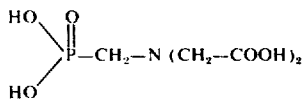

is mixed with water and an acid and heated to an elevated temperature. The oxidizing agent is then added and the iminodiacetic acid oxidativey converted into N-phosphonomethyl glycine and other decomposition products. The N-phosphonomethyl glycine is then isolated by precipitation, for example, by the addition of a water-miscible organic solvent.

The manner of reacting the N-(phosphonomethyl) iminodiacetic acid with the oxidizing agent is not critical and can be accomplished in many ways. For example, one can form an admixture of reactants and then heat the mixture to the temperature of reaction in a suitable vessel to convert the N-(phosphonomethyl) iminodiacetic acid to N-phosphonomethyl glycine. Alternatively, the oxidizing agent can be added to a mixture of N-(phosphonomethyl) iminodiacetic acid and acidified water which mixture has been preheated to the reaction temperature and the mixture continued to be heated at the elevated temperature to cause the oxidation and conversion of the N-(phosphonomethyl) iminodiacetic acid into N-phosphonomethyl glycine.

It is believed that the reaction takes place in accordance with the following equation:

The process of the instant invention is carried out in an acid media. Any of the organic or inorganic water-miscible or soluble acids can be employed in the process of this invention. It is preferred to employ those acids which themselves are not oxidized under the conditions of the reaction. The amount of the acid employed is not narrowly critical and can range from as low as 1 part acid per 100 parts of the N-(phosphonomethyl) iminodiacetic acid to 100 parts of acid per 1 part of N-(phosphonomethyl) iminodiacetic acid.

The time of reaction is not narrowly critical and can vary from as low as 1 minute heating time to as high as 40 or more hours. Of course, it is obvious to those skilled in the art that the yield of product will vary with the reaction time and the temperature of the reaction. For example, a short reaction time at low reaction temperatures, that is temperatures lower than about 70°C. would give very low yields of the product. It is preferred to conduct the instant reaction at a temperature of at least 70°C. and for a period of at least one hour to insure complete reaction and ease of recovery of the product.

The process of the instant invention can be conducted at atmospheric, sub-atmospheric or super-atmospheric pressure. In the case of the more volatile acids, it was of course apparent that one must conduct the present process at super-atmospheric pressure in order to keep the temperature within the above-defined limits. It is preferred to conduct the instant process at atmospheric pressure for ease of reaction and economics.

The acids that can be employed in the process of this invention include both the organic acids and the inorganic acids. The inorganic acids are, for example, sulfuric acid, hydrofluoric, phosphoric, fluorosulfonic, pyrophosphoric, nitric acid and the like. The organic acids which are useful in the present invention include the water-soluble or miscible organic acids and are for example, acetic, propionic, formic, mono-di- and tri-chloro acetic, mono-di- and trifluoroacetic, benzenesulfonic, p-toluene sulfonic, benzenephosphonic acid and the like.

The oxidizing agents which can be employed in the process of the instant invention include oxidizing

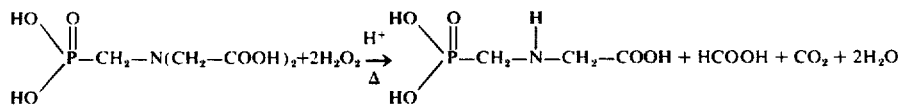

In conducting the process of this invention, the temperature of reaction can be from as low as 40° to 100°C. or even higher. It is preferred, for ease of reaction and to obtain the best yield of product, to conduct the process of this invention from about 70° to about 95°C.

The ratio of reactants, that is, the oxidizing agent and the N-(phosphonomethyl) iminodiacetic acid, is not narrowly critical. As is apparent from the above equation, for best yields and ease of recovery of the reaction product, that is the N-phosphonomethyl glycine, one should employ at least 2 moles of the oxidizing agent ($H_2O_2$) for each equivalent of the N-(phosphonomethyl) iminodiacetic acid. And preferably, to obtain the best yields, one employs at least three moles of the oxidizing agent for each mole of the N-(phosphonomethyl) iminodiacetic acid.

agents such as the inorganic peroxides, including hydrogen peroxide and organic peroxides. The organic peroxide oxidizing agents include tertiary-butylhydroperoxide, cumylhydroperoxide, peracetic acid, perbenzoic acid, peroxy trifluoroacetic acid, m-chloroperbenzoic acid, benzoyl peroxide, benzene persulfonic acid and the like. Other inorganic oxidizing agents include oxygen in the presence of metallic catalysts (Pt, Pd, Rh, etc.) or ultraviolet light, ozone, nitric acid, sodium hypochlorite, nitric oxide, lead tetra acetate, permanganic acid, dichromic acid, chlorine dioxide, persulfuric acid, perboric acid and the like.

The starting N-(phosphonomethyl) iminodiacetic acid starting material can be prepared by methods known in the art. For example, this material can be produced by the reaction of formaldehyde, iminodiacetic acid hydrochloride, and orthophosphorous acid in the presence of hydrochloric acid. The N-(phosphonomethyl) iminodiacetic acid mixture resulting from this reaction can be employed per se in the process of this invention or the N-phosphonomethyl) iminodiacetic acid can be isolated and then employed in the process of this invention.

The organic solvent which is employed in the isolation of the product of this invention is one of the water miscible organic solvents and may include alcohols such as methanol, ethanol isopropanol, butanol and the like, dioxane, and other water soluble heterocyclics; carboxylic acids such as acetic acid, propionic acid and the like; ketones such as acetone, methylethyl ketone and the like; glycols and polyglycols, for example ethylene glycol, propylene glycol, diethylene glycol, methyl cellosolve, dimethyl cellosolve, glycerol and the like. Many other water miscible organic solvents that can be employed in isolating the product of this invention will be apparent to those skilled in the art.

The compounds produced by the process of this invention are useful as herbicides and plant growth regulators.

The following examples serve to further illustrate the invention. All parts are parts by weight unless otherwise expressly set forth.

EXAMPLE 1

A mixture of N-(phosphonomethyl) iminodiacetic acid (13.7 grams, 0.06 mole), water (20 mls) and concentrated sulfuric acid (6.0 g., 0.06 mole) was heated with stirring at 82°–87°C. as 23 milliliters of 30% hydrogen peroxide was added dropwise over a two hour period. After the addition was complete, stirring was continued at 85°C. until a colorless solution was obtained. A nuclear magnetic resonance probe at this point of the reaction time indicated that a substantial amount of N-phosphonomethyl glycine was present with unreacted starting material. Therefore, an additional 5 milliliters of 30% hydrogen peroxide was added over a one hour period after which heating was continued for 4 hours at 82°–87°C. On cooling to room temperature, a white crystalline precipitate, identified as N-phosphonomethyl glycine, was formed. The reaction mixture was diluted with excess ethanol and stored overnight at approximately 37°C. in a refrigerator. The precipitated product was collected, washed with ethanol and diethyl ether and air dried. The yield of essentially pure white crystalline N-phosphonomethyl glycine was 7.8 grams. An additional 0.2 grams of the product was obtained on additional storage of the filtrate in the refrigerator. The purity of the product was determined by infrared and nuclear magnetic resonance spectra analysis

EXAMPLE 2

Thirty-nine parts of water and 39 parts of concentrated sulfuric acid were charged into a suitable reaction vessel and then 20 parts of N-(phosphonomethyl) iminodiacetic acid added. The mixture was heated to 80°C. and then 277 parts of a 35% hydrogen peroxide solution was added over a period of from 6½ to 7 hours while maintaining the temperature at 77°–81°C. During the addition of the hydrogen peroxide, additional N-(phosphonomethyl) iminodiacetic acid was added in 20 part increments over a 4 hour period. When visual observation showed the reaction mass was clear, that is, it contained no suspended solids, a sample was taken for nuclear magnetic resonance spectra analysis. The reaction was then continued to be heated at 80°C. with stirring until nuclear magnetic resonance spectra analysis showed that the reaction was essentially complete. The mixture was then cooled at 0°C. overnight, centrifuged, washed with a small amount of water and dried under vacuum to yield approximately 100 parts of N-phosphonomethyl glycine.

What is claimed is:

1. A process for the production of N-phosphonomethyl glycine which comprises reacting N-(phosphonomethyl)iminodiacetic acid with an oxidizing agent selected from the group consisting of hydrogen peroxide, nitric acid, sodium hypochlorite, nitric oxide, lead tetra acetate, permanganic acid, dichromic acid, chlorine dioxide, persulfuric acid, perboric acid, tertiary-butylhydroperoxide, cumylhydroperoxide, peracetic acid, perbenzoic acid, peroxy trifluoroacetic acid, m-chloroperbenzoic acid, benzoyl-peroxide and benzene persulfonic acid in an aqueous acidic media wherein the acid is selected from the group consisting of sulfuric, hydrofluoric, phosphoric, fluorosulfuric, pyrophosphoric, nitric, acetic, formic, propionic, moni, di and trichloroacetic, mono, di and trifluoroacetic, benzenesulfonic, p-toluenesulfonic and benzenephosphonic acid and at a temperature of from about 70° to about 100°C.

2. The process of claim 1 wherein the oxidizing agent is hydrogen peroxide.

3. The process of claim 1 wherein the acidic media is an organic acid media.

4. The process of claim 3 wherein the acid is formic acid.

5. The process of claim 4 wherein the oxidizing agent is hydrogen peroxide.

6. The process of claim 1 wherein the oxidizing agent is an organic oxidizing agent.

7. The process of claim 1 wherein the oxidizing agent is hydrogen peroxide and the acidic media is aqueous sulfuric acid.

8. The process of claim 7 wherein at least two equivalents of hydrogen peroxide is employed for each equivalent of N-phosphonomethyliminodiacetic acid.

9. The process of claim 1 wherein the time of reaction is at least 1 hour.

10. The process of claim 8 wherein the time of reaction is at least 1 hour.

* * * * *